United States Patent
Al-Sofi et al.

(10) Patent No.: US 11,774,436 B2
(45) Date of Patent: Oct. 3, 2023

(54) METHOD FOR DETERMINING FOAM STABILITY IN A CORE PLUG

(71) Applicant: Saudi Arabian Oil Company, Dhahran (SA)

(72) Inventors: Abdulkareem M. Al-Sofi, Dhahran (SA); Jinxun Wang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 24 days.

(21) Appl. No.: 17/554,110

(22) Filed: Dec. 17, 2021

(65) Prior Publication Data
US 2023/0194497 A1 Jun. 22, 2023

(51) Int. Cl.
*G01N 33/24* (2006.01)
*C09K 8/60* (2006.01)
*G01N 13/02* (2006.01)

(52) U.S. Cl.
CPC .............. *G01N 33/24* (2013.01); *C09K 8/602* (2013.01); *G01N 2013/025* (2013.01)

(58) Field of Classification Search
CPC ... G01N 33/24; G01N 2013/025; C09K 8/602
See application file for complete search history.

(56) References Cited

U.S. PATENT DOCUMENTS 2,345,935 A * 4/1944 Hassler .............. G01N 15/0826
73/38
5,261,267 A 11/1993 Kamath et al.
5,493,226 A * 2/1996 Honarpour ............ E21B 49/005
73/152.14
7,805,982 B2 10/2010 Hilab
10,689,978 B2 6/2020 Al-Sofi et al.
10,845,322 B2 * 11/2020 Adebayo .............. G01N 24/081
2019/0368349 A1 12/2019 Al-Sofi et al.
2021/0355374 A1* 11/2021 Tayyib .................... C09K 8/82

OTHER PUBLICATIONS

AlSofi et al. "Portrayal and Demonstration of a Novel Procedure for In-Situ Estimation of Gelation Time" IOR 2019—20th European Symposium on Improved Oil Recovery Apr. 8-11, 2019, Pau, France, 8 pgs.
Isaacs et al. "Investigation of Foam Stability in Porous Media at Elevated Temperatures" SPE Reservoir Engineering, May 1988, 8 pgs.
McPhee et al. "Foam Flooding of Cores Under North Sea Reservoir Conditions" SPE/DOE 17360, 1988, 15 pgs.

* cited by examiner

*Primary Examiner* — Ryan D Walsh
(74) *Attorney, Agent, or Firm* — DINSMORE & SHOHL LLP

(57) ABSTRACT

A method of determining foam stability includes placing a core plug and two porous plates into a core holder of a vesselcore plug. The first porous plate and the second porous plate are disposed on opposite sides of the core plug, and the core plug, the first porous plate, and the second porous plate are saturated with surfactant. The method further includes alternating surfactant solution injections between a first injection area located on the first porous plate and a second injection area located on the second porous plate, while ensuring that the surfactant solution is being continuously fed, thereby forming continuously flowing foam in-situ within the core plug, in which the surfactant solution comprises gas and the surfactant; and monitoring the pressure drop to determine the stability of the foam in the core plug.

19 Claims, 2 Drawing Sheets

METHOD FOR DETERMINING FOAM STABILITY IN A CORE PLUG

TECHNICAL FIELD

The present disclosure relates to determining foam stability in a core plug of a geologic formation, usually reservoir rock, taken during or after drilling a well.

BACKGROUND

Economic and efficient oil and gas production is dependent on understanding key properties of reservoir rock and fluid, such as porosity, permeability, compressibility, wettability, formation flow potential, fracture orientation, and fluid compatibility. Geoscientists have developed a variety of approaches, including log and core analysis techniques, to measure these properties. Core analysis is especially important in geologic formations with vertical and lateral heterogeneity. Core analysis can include evaluation of rock properties and anisotropy; organic matter content, maturity, and type; fluid content; fluid sensitivity; and geomechanical properties. This information can be used to calibrate log and seismic measurements and to help in well and completion design, well placement, and other aspects of reservoir production.

SUMMARY

Conventional methods for determining foam performance and foam stability cannot give an accurate measurement of foam performance and foam stability in situ. For example, the conventional bulk foam test is often conducted at ambient pressure, and the interactions between the foam and reservoir rock are not involved. In order to determine in situ foam stability, large core plugs are needed and specialized coreholding setups, which must be used, are not commercially-available. Conventional coreholding setups cannot be used due to the large size of the core plugs. Therefore, a need exists for a method for accurately determining foam performance and foam stability in a core plug at in situ conditions utilizing commercially-available coreholders.

In accordance with one embodiment of the present disclosure, a method of determining foam stability includes placing a core plug, a first porous plate, and a second porous plate into a core holder, in which: the first porous plate and the second porous plate are disposed on opposite sides of the core plug, and the core plug, the first porous plate, and the second porous plate are saturated with surfactant before the generation or injection of the foam. The method also includes alternating surfactant solution injections between a first injection area located on the first porous plate and a second injection area located on the second porous plate, while ensuring that the surfactant solution is being continuously fed to the core plug, thereby forming continuously flowing foam in-situ within the core plug, in which the surfactant solution comprises gas and the surfactant; and monitoring the pressure drop across the core plug during the alternating injection of the surfactant solution to determine the stability of the foam in the core plug. A commercially-available coreholder may be used for this method as the core plug is a size that may be tested using a commercially-available coreholder.

Additional features and advantages of the described embodiments will be set forth in the detailed description which follows. The additional features and advantages of the described embodiments will be, in part, readily apparent to those skilled in the art from that description or recognized by practicing the described embodiments, including the detailed description which follows as well as the drawings and the claims.

BRIEF DESCRIPTION OF THE SEVERAL VIEWS OF THE DRAWING

The following detailed description of specific embodiments of the present disclosure can be best understood when read in conjunction with the following drawing, where like structure is indicated with like reference numerals and in which.

DETAILED DESCRIPTION

Figure 1:
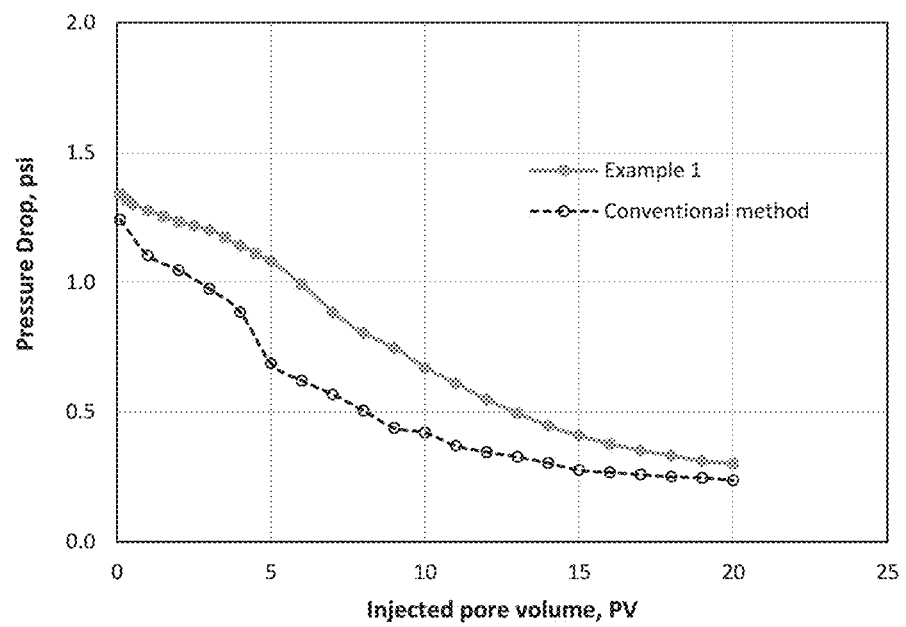
FIG. 1 graphically depicts the relationship between the pressure drop (y-axis) and injected pore volume (x-axis) during foam stability testing, according to one or more embodiments described in this disclosure.

As used throughout this disclosure, the term "coreflooding" refers to a test in which a fluid or combination of fluids is injected into a core plug. Objectives include measurement of permeability, relative permeability, saturation change, formation damage caused by the fluid injection, or interactions between the fluid and the rock, such as the foam stability of the fluid. The core material often comes from an oil reservoir, but some tests use outcrop rock. The fluid in place at the start of the test is typically either a simulated formation brine, oil, or a combination of brine and oil. Injected fluids may include crude oil, simulated reservoir brine, refined fluids, drilling mud filtrate, acids, foams, surfactant solutions, or other chemicals used in the oil field. Pressures and flow rates at both ends of the core are measured.

As used throughout this disclosure, the term "coreflooding coreholder" refers to a coreholder vessel equipped to conduct coreflooding experiments and measurements, including coreflooding foam stability testing.

As used throughout this disclosure, the term "coreholder" refers to a vessel designed to withstand elevated temperatures and pressures, such as up to 20,000 pounds per square inch (psi) (137,895 kilopascals (kPa); 1 psi=6.89476 kPa) and 300° C., and to test core plugs at these elevated temperatures and pressures.

As used throughout this disclosure, the term "core plug" refers to a plug, or sample, taken from a whole core from a formation for analysis. Core plugs are conventionally 1 to 1.5 in. (2.5 to 3.8 centimeters (cm); 1 in.=2.54 cm) in diameter and 1 to 12 inches (in.) (2.5 to 30 cm) long. Core plugs are conventionally cut perpendicular to the axis of the core or parallel to the axis, which form horizontal and vertical plugs, respectively, when cut from a vertical wellbore. Conventional core plug analysis is conducted in a coreholder.

As used throughout this disclosure, the term "formation" refers to a body of rock that is sufficiently distinctive and continuous from the surrounding rock bodies that the body of rock can be mapped as a distinct entity. A formation is, therefore, sufficiently homogenous to form a single identifiable unit containing similar rheological properties throughout the formation, including, but not limited to, porosity and permeability. A formation is the fundamental unit of lithostratigraphy.

As used throughout this disclosure, the term "pore volume" refers to the ratio of a porous material's void space to a porous material's total bulk volume.

As used throughout this disclosure, the term "reservoir" refers to a subsurface formation having sufficient porosity and permeability to store and transmit fluids.

As used throughout this disclosure, the term "saturated" refers to the almost complete filling (such as 0.6 pore volume (PV), 0.8 PV, 0.9 PV, 0.95 PV, or 0.99 PV or above) of the core sample pore volume with a given fluid.

As used throughout this disclosure, the term "whole core" refers to a complete section of a conventionally-drilled core. The section may be up to approximately 2 feet ((60 cm); 1 foot=30.48 cm) in length, with conventional core diameters lying between 1.75 and 5.25 in. (4.4 and 13.3 cm).

The present disclosure is directed to methods for determining foam stability in core plugs at in situ conditions. The stability of foam makes it possible to effectively reduce the mobility of displacing gas, steam or water, thereby improving the sweeping efficiency in oil reservoirs. The method includes placing a core plug 102 and two porous plates 104/106 into a core holder 100 of a vessel. The vessel may be a commercially-available coreholder, and the core plug may be substantially cylindrical in shape.

Figure 2:
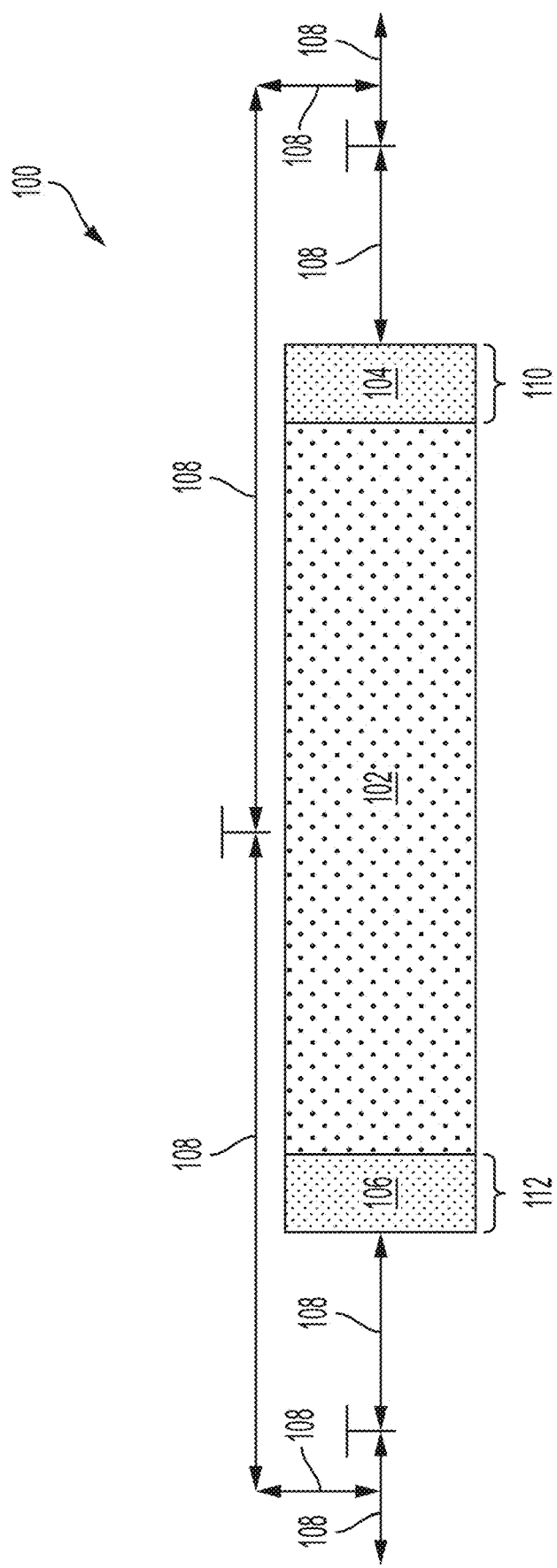
FIG. 2 is an illustration of the core holder according to one or more embodiments described herein.

Now referring to FIG. 2, the first and second porous plates 104/106 are disposed on opposite sides of the core plug 102. Specifically, the first and second porous plates 104/106 may each couple to each respective end of the core plug. The flat surfaces of the core plug 102 and the first porous plate 104 may be coupled together on one end of the core plug 102, and the flat surfaces of the core plug 102 and the second porous plate 106 may be coupled together on the opposite end of the core plug 102. The foam can be in-situ generated by co-injecting gas and surfactant into the core, or an externally formed foam can be injected into the surfactant-saturated core. The diameter, porosity, and permeability of the first porous plate may be within 0.1%, 0.5%, 1%, 2%, or 5% of a diameter, porosity, and permeability of the second porous plate. The core plug may be saturated with the surfactant solution 108 and the first porous plate 104 and the second porous plate 106 may be saturated with the surfactant prior to the injection of surfactant solution into the core plug 102.

The method further includes alternating surfactant solution 108 injections between a first injection area 110 located on the first porous plate 104 and a second injection area 112 located on the second porous plate 106, while ensuring that the surfactant solution 108 is being continuously fed to the core plug 102 thereby forming continuously flowing foam in-situ within the core plug 102. The surfactant solution 108 comprises gas and the surfactant. The injection areas 110/112 may include a point on, a part of, or the entirety of the exposed end, face, or surface of the first or second porous plates 104/106. The surfactant solution 108 may be injected in an injection point or may be injected along the entire exposed face of the first or second porous plate 104/106. Lastly, the method includes monitoring the pressure drop, or pressure profile change, across the core plug 102 during the alternating injections of the surfactant solution 108 to determine the stability of the foam in the core plug 102. The foam stability is determined through monitoring the pressure response while the surfactant solution 108 resides in the core plug 102. In-situ foam stability can be determined using normal length core or core composite, with conventional coreholders 100, and without the need for multiple pressure taps.

To determine foam stability in the core plugs at in situ conditions, the method may be conducted at in situ confining pressure and temperature. Confining pressure, or geostatic pressure, is the pressure of the weight of overburden, or overlying rock, on a formation. The confining pressure and temperature will vary depending on the depth, type of formation, and reservoir conditions meant to be simulated. The net confining pressure may be from 200 to 5000 psi (1379 to 34474 kPa), from 300 to 2500 psi (2068 to 17237 kPa), from 500 to 2000 psi (3447 to 13790 kPa), or from 800 to 1500 psi (5516 to 10342 kPa). The temperature may be from 10 to 150° C., from 80 to 125° C., from 90 to 115° C., or from 95 to 110° C. The method may further be conducted with a specific backpressure. Backpressure is the pressure opposed to the desired flow of liquids registered on testing equipment. The backpressure may be from 0 to 5000 psi (0 to 34474 kPa), from 25 to 1000 psi (172.36 to 6894.76 kPa), from 25 to 450 psi (172.36 to 3102.64 kPa), from 50 to 350 psi (344.738 to 2413.17 kPa), from 80 to 300 psi (551.58 to 2068.43 kPa), or from 100 to 250 psi (689.476 to 1723.69 kPa).

The surfactant solution same as that used for generating foam is injected into the core plug where pressures are monitored to observe foam stability with conventional coreholders, and without the need for pressure taps. The differential pressure between the upstream and downstream side of the core is monitored. The pressures are measured at downstream of the injection areas and upstream of the injection areas.

Various surfactant components are contemplated and may include anionic, cationic, amphoteric, or nonionic surfactants, and any combinations of them. Non-limiting examples of anionic surfactants include petroleum sulfonate, alcohol alkoxy sulfate, alpha olefin sulfonate, ethoxyl alcohol ether sulfates, internal olefin sulfonate, or combinations of these. Non-limiting examples of cationic surfactants include cetyl trimethyl ammonium bromide (CTAB), dodecyl trimethyl ammonium bromide (DTAB), ethoxylated alkyl amine, alkanol amides, or combinations of these. Non-limiting examples of nonionic surfactants include amine oxides, alcohol ethoxylates, alkyl-phenol ethoxylates, aykyl ethoxy carboxylate, or combinations of these. Non-limiting examples of amphoteric surfactants include alkyl betaine, cocoamidopropyl betaine, amphoteric alkyl amine, or combinations of these. The surfactant may include at least one of alpha olefin sulfonate, ethoxyl alcohol ether sulfates, ethoxylated alkyl amine, amphoteric alkyl amine, amine oxides, or alcohol ethoxylates.

As previously stated, the surfactant solution includes both a surfactant and gas. In embodiments, the gas may include nitrogen ($N_2$), hydrocarbon gas, carbon dioxide ($CO_2$), or combinations thereof. The surfactant solution may include from 60 to 99 vol. %, from 65 to 99 vol. %, from 70 to 99 vol. %, from 75 to 99 vol. %, from 80 to 99 vol. %, from 85 to 99 vol. %, from 90 to 99 vol. %, from 95 to 99 vol. %, from 60 to 95 vol. %, from 65 to 95 vol. %, from 70 to 95 vol. %, from 75 to 95 vol. %, from 80 to 95 vol. %, from 85 to 95 vol. %, from 90 to 95 vol. %, from 60 to 90 vol. %, from 65 to 90 vol. %, from 70 to 90 vol. %, from 75 to 90 vol. %, from 80 to 90 vol. %, from 85 to 90 vol. %, from 60 to 85 vol. %, from 65 to 85 vol. %, from 70 to 85 vol. %, from 75 to 85 vol. %, from 80 to 85 vol. %, from 60 to 80 vol. %, from 65 to 80 vol. %, from 70 to 80 vol. %, from 75 to 80 vol. %, from 60 to 75 vol. %, from 65 to 75 vol. %, from 70 to 75 vol. %, from 60 to 70 vol. %, from 65 to 70 vol. %, or from 60 to 65 vol. % gas.

The method may further include saturating the core plug and the porous plates with an aqueous solution. The aqueous solution may include one or more than one of fresh water, salt water, brine, connate brine, municipal water, formation water, produced water, well water, filtered water, distilled water, and sea water. In some embodiments, the aqueous solution may include water or a solution containing water and one or more inorganic compounds dissolved in the water or otherwise completely miscible with the water. In some embodiments, the aqueous solution may contain brine, including natural and synthetic brine. Brine includes water and a salt that may include calcium chloride, calcium bromide, sodium chloride, sodium bromide, other salts, and combinations of these. The aqueous solution may include total dissolved solids of from 150,000 to 300,000 mg/L (150 to 300 kg/m$^3$).

In embodiments, the method may further include determining a base pressure drop, in which the base pressure drop comprises the pressure drop after saturating the core plug with the aqueous solution and before the core plug is saturated with the surfactant. The method may further include calculating a resistance factor from the pressure drop during the foam flowing in the core and the base pressure drop, in which the resistance factor ranges from 1 to 10,000, from 1 to 100, from 2 to 100, from 5 to 100, from 2 to 200, from 2 to 500, from 2 to 1000, from 5 to 200, from 5 to 1000, from 5 to 2000, from 5 to 5000, from 10 to 1000, from 10 to 2000, from 10 to 5000, from 10 to 10000, from 5 to 10, from 5 to 9, from 5 to 8, from 5 to 7, from 5 to 6, from 6 to 10, from 6 to 9, from 6 to 8, from 6 to 7, from 7 to 10, from 7 to 9, from 7 to 8, from 8 to 10, from 8 to 9, or from 9 to 10.

The method may further include calculating a residual resistance factor from the base pressure drop and the pressure drop after the foam placement, in which the resistance factor ranges from 1 to 10, from 1 to 9, from 1 to 8, from 1 to 7, from 1 to 6, from 1 to 5, from 1 to 4, from 1 to 3, from 1 to 2, from 2 to 10, from 2 to 9, from 2 to 8, from 2 to 7, from 2 to 6, from 2 to 5, from 2 to 4, from 2 to 3, from 3 to 10, from 3 to 9, from 3 to 8, from 3 to 7, from 3 to 6, from 3 to 5, from 3 to 4, from 4 to 10, from 4 to 9, from 4 to 8, from 4 to 7, from 4 to 6, from 4 to 5, from 5 to 10, from 5 to 9, from 5 to 8, from 5 to 7, from 5 to 6, from 6 to 10, from 6 to 9, from 6 to 8, from 6 to 7, from 7 to 10, from 7 to 9, from 7 to 8, from 8 to 10, from 8 to 9, or from 9 to 10.

The method further includes alternating surfactant solution injections between a first injection area located on the first porous plate and a second injection area located on the second porous platecore plug. It is contemplated that ensuring that the surfactant solution is being continuously fed to the core plug results in preventing the dilution of the effective components within the surfactant solution and ensuring that the foam is continuously flowing within the core plug. The gas is maintained in the core by the porous plates at both ends. The surfactant solution may be injected in an injection point or may be injected along the entire exposed face, or surface, of the first or second porous plate. Each alternating surfactant solution injection may include injecting up to 1 PV, up to 0.9 PV, up to 0.8 PV, up to 0.75 PV, up to 0.7 PV, up to 0.6 PV, up to 0.5 PV, up to 0.4 PV, up to 0.25 PV, up to 0.2 PV, up to 0.15 PV, up to 0.1 PV, up to 0.08 PV, or up to 0.05 PV of the core plug per injection. Although the foam composition may not be changed if injecting from one end only, it is preferred to inject in alternating directions and keep a minimum injection amount in each cycle. This will keep most part of the original foam components in the core, and minimize the introduction of fresh component, which helps maintain more representative foam in the core for stability evaluation. Without being limited by theory, this pore volume may be approximately equivalent to 0.5 PV of the core plug. To avoid replacing too much surfactant in the core, no more than 0.5 PV, 0.4 PV, 0.3 PV, 0.25 PV, 0.2 PV, 0.15 PV, 0.1 PV, 0.08 PV, or 0.05 PV of the core plug may be injected. This value may alternatively be expressed as no more than 1 PV, 0.8 PV, 0.6 PV, 0.5 PV, 0.4 PV, 0.3 PV, 0.2 PV, 0.16 PV, or 0.1 PV of the first or second porous plate.

In another embodiment, each alternating surfactant solution injection may include injecting equal amounts of surfactant in each injection. It is contemplated that alternating surfactant solution injections further includes injecting the surfactant at a constant flow rate, which may be from 0.01 to 1.0 milliliter per minute (ml/min) (0.00017 to 0.0167 cubic centimeters per second (cc/s); 1 ml/min=0.0167 cc/s), from 0.8 to 0.15 ml/min (0.0013 to 0.0025 cc/s), or 0.1 ml/min (0.00167 cc/s).

Alternating the surfactant solution injections while ensuring the surfactant solution is being continuously fed to the core plug allows for continuous, but alternating, flow of the surfactant solution within the core plug. The porous plates on both ends of the core plug ensure that the surfactant solution remains within the core plug, so that the measured foam stability is an accurate foam stability for the surfactant solution in the porous media of the core plug. By continuously injecting the surfactant solution, the testing method more accurately simulates in situ surfactant solution injection conditions. When a surfactant solution is injected downhole into a formation, the surfactant solution is being continuously pumped into the formation, meaning that the surfactant solution is in a state of constant flow. Therefore, continuously injecting the surfactant solution into the core plug more accurately simulates in situ foam formation, resulting in a more accurate measurement of foam stability.

Constant flow in a porous medium provides mixing and agitation to the surfactant solution. The continuous flow of this method better replicates the in situ condition of pumping the surfactant solution into a formation by simulating constant flow, therefore more accurately measuring the foam stability and generating more representative data.

EXAMPLE

The following example illustrates features of the present disclosure but is not intended to limit the scope of the disclosure.

Example 1

A nonionic surfactant, NEODOL 25-12 alcohol ethoxylate (a blend of C12 to C15 high purity, lightly branched, primary alcohols with an average of approximately 12 moles of ethylene oxide per mole of alcohol, available from Shell Chemicals, headquartered in Houston, Tex.), was used as the foaming agent in this example. A synthetic seawater with a total dissolved solids (TDS) of 57,670 mg/L was used to prepare the surfactant solution. Detailed brine composition is presented in Table 1. The surfactant solution included 0.5 wt. % NEODOL 25-12 and 99.5 wt. % synthetic seawater.

TABLE 1

Synthetic seawater composition.

| | |
|---|---|
| Na+, mg/L | 18,300 |
| Ca2+, mg/L | 650 |
| Mg2+, mg/L | 2,110 |
| Cl−, mg/L | 32,200 |
| HCO3−, mg/L | 120 |
| SO4−, mg/L | 4,290 |
| TDS, mg/L | 57,670 |

A carbonate core plug was used in the coreflooding test to demonstrate the foam stability evaluation method. The core sample was first fully saturated with the brine, and then loaded into a FDES-645 coreflooding system available from Coretest Systems, Inc., USA for the foam evaluation test. The coreflooding test was conducted at 60° C., 1000 psi backpressure and 2000 psi confining pressure. All the tests were performed at a constant flow rate of 0.5 ml/min.

The brine was first injected into the core sample to determine the baseline pressure drop before the foam placement, and then the core sample was flushed with the 0.5 wt % surfactant solution to satisfy adsorption. After that, the foam was in-situ generated by co-injecting surfactant and nitrogen gas at a constant rate ratio, where the surfactant was injected at 0.1 ml/min (milliliter per minute) and nitrogen gas was injected at 0.4 ml/min. This injection corresponded to 80 vol. % gas by volume of surfactant and nitrogen gas injected, meaning 80 vol. % foam quality. The foam quality of 80% was prepared in this example. Foam quality is the volume percentage of gas in the foam system at a given pressure and temperature condition. The pressure drop across the core sample was recorded to calculate the resistance factor (RF):

$$RF = \frac{\Delta P_f}{\Delta P_b} \quad (1)$$

where $\Delta P_f$ is the pressure drop during foam injection process, and the $\Delta P_b$ is the base case pressure drop before foam injection (when only water is injected).

The baseline pressure drop during the brine injection is 0.16 psi. During the co-injection of the surfactant solution solution and nitrogen gas, the average pressure drop is around 1.2 psi. From Equation (1), the calculated resistance factor of this example test is 7.5.

After the foam was generated in the core sample, foam stability was then evaluated. The pressure drop across the core sample was recorded, and the residual resistance factor (RRF) can be calculated as:

$$RRF = \frac{\Delta P_{post-foam}}{\Delta P_b} \quad (2)$$

where $\Delta P_{post-foam}$ is the pressure drop after the foam placement.

For comparison, a conventional method was also used to evaluate the foam stability. After the foam generated in the core by co-injecting the surfactant solution and nitrogen gas with the same foam quality of 80%, brine was then injected without the use of porous plate. Similarly, the pressure drop was recorded for calculating RRF.

FIG. 1 shows the pressure responses measured by these two methods. The RRF can be calculated from these pressure results, which will exhibit the same decreasing trends as these pressure curves. Table 2 presents the pressure and RRF data. Results show that using the new foam evaluation method, the RRF or the measured pressure (the solid line in FIG. 1) decreases much slower than that when using the conventional method. For example, by the new evaluation method, the RRF will drop to 50% of its original value after 10 pore volumes (PV) of fluid injection (post foam placement). If using the conventional method, after 6.0 PV of fluid injection the RRF can decrease to 50% of its original value. This indicates that the present foam stability evaluation method provides a more accurate foam stability measurement than the conventional method. When using the conventional method, the gas can be more easily flushed out by the brine injection, especially when using a short core sample for the test. In the actual reservoir, the pore volume is extremely large. Therefore, the in-situ generated foam tends to propagate a long distance in the reservoir with a relatively stable foam composition. By using a porous plate to keep the gas in the core sample, the new evaluation method can provide a more representative result of foam stability evaluation.

TABLE 2

Foam stability test results.

| Conventional Method | | | New method | | |
|---|---|---|---|---|---|
| Inj. Pore Vol. PV | DP psi | RRF | Inj. Pore Vol. PV | DP psi | RRF |
| 0.1 | 1.24 | 7.75 | 0.1 | 1.34 | 8.38 |
| 1.0 | 1.10 | 6.90 | 1.0 | 1.27 | 7.97 |
| 3.0 | 0.97 | 6.09 | 3.0 | 1.20 | 7.51 |
| 6.0 | 0.62 | 3.88 | 6.0 | 0.99 | 6.19 |
| 10 | 0.42 | 2.63 | 10 | 0.67 | 4.19 |
| 15 | 0.28 | 1.72 | 15 | 0.41 | 2.55 |
| 20 | 0.24 | 1.48 | 20 | 0.30 | 1.89 |

For the purposes of describing and defining the present method, it is noted that reference in this application to a characteristic of the subject matter of the present disclosure being a "function of" a parameter, variable, or other characteristic is not intended to denote that the characteristic is exclusively a function of the listed parameter, variable, or characteristic. Rather, reference in this application to a characteristic that is a "function" of a listed parameter, variable, etcetera, is intended to be open ended such that the characteristic may be a function of a single parameter, variable, etcetera, or a plurality of parameters, variables, etcetera.

It is also noted that recitations in this application of "at least one" component, element, etcetera, should not be used to create an inference that the alternative use of the articles "a" or "an" should be limited to a single component, element, etcetera.

For the purposes of describing and defining the present method it is noted that the term "approximately" is utilized in this application to represent the inherent degree of uncertainty that may be attributed to any quantitative comparison, value, measurement, or other representation. The term "approximately" is also utilized in this application to represent the degree by which a quantitative representation may vary from a stated reference without resulting in a change in the basic function of the subject matter at issue.

Having described the subject matter of the present disclosure in detail and by reference to specific embodiments, it is noted that the various details disclosed in this application should not be taken to imply that these details relate to elements that are essential components of the various embodiments described in this application, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified in this application as preferred or particularly advantageous, it is contemplated that the present disclosure is not necessarily limited to these aspects.

What is claimed is:

1. A method of determining foam stability comprising:
   placing a core plug, a first porous plate, and a second porous plate into a core holder, in which:
      the first porous plate and the second porous plate are disposed on opposite sides of the core plug, and
      the core plug, the first porous plate, and the second porous plate are saturated with surfactant;
   alternating surfactant solution injections between a first injection area located on the first porous plate and a second injection area located on the second porous plate, while ensuring that the surfactant solution is being continuously fed to the core plug, thereby forming continuously flowing foam in-situ within the core plug, in which the surfactant solution comprises gas and the surfactant; and
   monitoring the pressure drop across the core plug during the alternating injection of the surfactant solution to determine the stability of the foam in the core plug.

2. The method of claim 1, further comprising calculating a resistance factor from the pressure drop, in which the resistance factor ranges from 1 to 10,000.

3. The method of claim 1, in which the gas comprises nitrogen, hydrocarbon, carbon dioxide, or combinations thereof.

4. The method of claim 1, in which the surfactant solution comprises from 60% to 99% gas.

5. The method of claim 1, in which ensuring that the surfactant solution is being continuously fed to the core plug results in maintaining gas concentration within the surfactant solution and ensuring that the foam is continuously flowing within the core plug.

6. The method of claim 1, in which alternating surfactant solution injections and monitoring the pressure drop across the core plug are conducted at a confining pressure of from 200 to 5000 psi.

7. The method of claim 1, in which alternating surfactant solution injections and monitoring the pressure fluctuation of the core plug are conducted with a backpressure of from 0 to 5000 psi.

8. The method of claim 1, in which alternating surfactant solution injections and monitoring the pressure drop across the core plug are conducted at a temperature of from 10° C. to 150° C.

9. The method of claim 1, further comprising saturating the core plug and porous plates with an aqueous solution.

10. The method of claim 9, further comprising saturating the core plug with the surfactant solution and displacing the aqueous solution.

11. The method of claim 9, further comprising saturating the first and second porous plates with the surfactant and displacing the aqueous solution.

12. The method of claim 9, further comprising determining a base pressure drop, in which the base pressure drop comprises the pressure drop after saturating the core plug with the aqueous solution and before the core plug is saturated with the surfactant.

13. The method of claim 12, further comprising calculating a resistance factor from the pressure drop during surfactant solution injection and the base pressure drop, in which the resistance factor ranges from 1 to 10,000.

14. The method of claim 1, in which alternating surfactant solution injections further comprises injecting up to 0.5 pore volume of the core plug per injection.

15. The method of claim 1, in which alternating surfactant solution injections further comprises:
   injecting up to 0.5 pore volume of the core plug per injection into the first porous plate; and
   injecting up to 0.5 pore volume of the core plug per injection into the second porous plate.

16. The method of claim 1, in which alternating surfactant solution injections further comprises injecting up to 0.2 pore volume of the core plug per injection.

17. The method of claim 1, in which alternating surfactant solution injections further comprises injecting equal amounts of surfactant in each injection.

18. The method of claim 1, in which alternating surfactant solution injections further comprises injecting the surfactant at a constant flow rate ranging from 0.1 to 1.0 ml/m.

19. The method of claim 1, in which the first porous plate comprises a diameter, porosity, and permeability within 0.1% of a diameter, porosity, and permeability of the second porous plate.

* * * * *